US012788603B2

(12) United States Patent
Hörig et al.

(10) Patent No.: US 12,788,603 B2
(45) Date of Patent: Nov. 10, 2026

(54) ORTHOSIS

(71) Applicant: OTTO BOCK HEALTHCARE GMBH, Vienna (AT)

(72) Inventors: Viktor Gerhard Hörig, Vienna (AT); Roland Auberger, Vienna (AT); Matthias Vollbrecht, Vienna (AT); Dirk Seifert, Vienna (AT); Etienne Overdevest, Vienna (AT); Laura Hoffsümmer, Vienna (AT)

(73) Assignee: OTTO BOCK HEALTHCARE GMBH, Vienna (AT)

( * ) Notice: Subject to any disclaimer, the term of this patent is extended or adjusted under 35 U.S.C. 154(b) by 187 days.

(21) Appl. No.: 18/292,530

(22) PCT Filed: Jul. 25, 2022

(86) PCT No.: PCT/EP2022/070811
§ 371 (c)(1),
(2) Date: Jan. 26, 2024

(87) PCT Pub. No.: WO2023/006674
PCT Pub. Date: Feb. 2, 2023

(65) Prior Publication Data

US 2024/0341990 A1 Oct. 17, 2024

(30) Foreign Application Priority Data

Jul. 28, 2021 (DE) .................... 10 2021 119 666.3

(51) Int. Cl.
*A61F 5/01* (2006.01)

(52) U.S. Cl.
CPC ............ *A61F 5/013* (2013.01); *A61F 5/0193* (2013.01); *A61F 2005/0137* (2013.01); *A61F 2005/0155* (2013.01)

(58) Field of Classification Search
CPC .................... A61F 5/013; A61F 5/0193; A61F 2005/0137; A61F 2005/0155; A61F 2005/0134; A61F 5/0123
See application file for complete search history.

(56) References Cited

U.S. PATENT DOCUMENTS 5,421,810 A * 6/1995 Davis .................... A61F 5/0193 602/26
6,387,066 B1 * 5/2002 Whiteside ............ A61F 5/0123 602/26
(Continued)

FOREIGN PATENT DOCUMENTS

DE 20 2015 102 008 U1 6/2015
DE 102016108183 A1 * 11/2017 ........... A61F 5/0125
(Continued)

*Primary Examiner* — Tarla R Patel
(74) *Attorney, Agent, or Firm* — WCF IP

(57) ABSTRACT

The invention relates to an orthosis comprising: a first fastening element (15) for fastening a first orthosis component (10) to a proximal body part of a user; a second orthosis component (20) having a second fastening element (21) for being fixed to a distal body part of the user; and a joint device (30) which is located at the proximal end (22) of the second orthosis component (20) and which has a joint upper part (40) and which makes it possible for the second orthosis component (20) to pivot about a joint axis (4) in the sagittal plane relative to the joint upper part (40), the joint upper part (40) being mounted or designed on the first orthosis component (10) in a fastening device (11) so as to be pivotable and/or displaceable in the frontal plane and so as to be rotationally rigid in the sagittal plane.

15 Claims, 10 Drawing Sheets

(56) References Cited

U.S. PATENT DOCUMENTS

| | | | | |
|---|---|---|---|---|
| 6,666,837 | B2 * | 12/2003 | Weihermuller | A61F 5/0123 602/26 |
| 11,179,288 | B2 | 11/2021 | Tuttemann et al. | |
| 11,612,507 | B2 * | 3/2023 | Snow | A61F 7/10 602/2 |
| 2006/0015049 | A1 * | 1/2006 | Suarez | A61F 5/0193 602/23 |
| 2007/0276305 | A1 * | 11/2007 | Kahlmeyer | A61F 5/0123 602/26 |
| 2009/0043232 | A1 | 2/2009 | Borschneck | |
| 2017/0196721 | A1 | 7/2017 | Yun | |
| 2019/0328604 | A1 * | 10/2019 | Contreras-Vidal | A61H 1/0244 |
| 2020/0069452 | A1 | 3/2020 | Snow | |
| 2020/0113721 | A1 * | 4/2020 | Kilbey | A61F 7/00 |
| 2021/0085502 | A1 * | 3/2021 | Sima | A61F 5/0102 |

FOREIGN PATENT DOCUMENTS

| | | | |
|---|---|---|---|
| DE | 10 2017 121 343 | A1 | 3/2019 |
| EP | 2 959 869 | A1 | 12/2015 |
| WO | 2015/197704 | A1 | 12/2015 |

* cited by examiner 14
14

11
410
14
41

11
41
14
11
41
14

11
14
4
32
41
40
42
30

ORTHOSIS

The invention relates to an orthosis having a first fastening element for fastening a first orthosis component on a proximal body part of a user, a second orthosis component having a second fastening element for fastening on a distal body part of the user, and a joint device arranged on the proximal end of the second orthosis component, which has an upper joint part and allows pivoting of the second orthosis component in the sagittal plane relative to the upper joint part about a joint axis. The orthosis is configured in particular as a hip orthosis or shoulder orthosis.

Orthoses are orthopedic aids which are fitted on an existing limb and guide, restrict or assist the movements. Drives or resistance devices may be arranged between components connected to one another in an articulated fashion, and these may be adjusted or set. The adjustment may be carried out on the basis of sensor data which are communicated to a data processing device. In the scope of this application, the term orthosis is also intended to include exoskeletons which are fitted on the body of a patient and form an outer supporting structure, particularly in order to guide and influence the movements of a user, for example assisting these movements by drives or braking them by means of resistance devices. Besides assisting everyday tasks, orthoses and exoskeletons as specific cases thereof may also be used and fitted for training purposes or therapeutic purposes.

The securing of orthoses is carried out by means of fastening devices or fastening elements, which are arranged on shells, rods or struts. The shells, rods or struts are generally connected to one another in an articulated fashion or resiliently mounted on one another. For fastening and secure fit of the orthoses on the respective limb or the torso, shells or buckles are provided, which at least partially enclose the limb and are positioned firmly on the limb or the torso by means of clasps, belt fasteners, clips or the like.

Particularly in the cases of orthoses on joints which can be deflected in more than one plane, the guiding of the respective joint axis or the joint axes is important and sometimes difficult to perform. For example, the hip or shoulder joint is a ball joint whose center of joint lies inside the body, which makes exact alignment of the axis of an external joint more difficult. However, a good alignment of the joint axes is necessary in order to ensure comfortable seating and good force transmission of the orthosis, and to avoid relative movements.

WO 2015-197704 A1 discloses a leg orthosis having a fastening device for securing the leg orthosis on a torso of the orthosis user and at least one joint device, by means of which a first orthosis component that can be secured on an extremity of the orthosis user is mounted to be pivotable relative to the fastening device. The joint device has at least three joints which respectively have at least one pivot axis, these pivot axes intersecting at a common point.

It is an object of the present invention to provide an orthosis with which simplified and improved guiding of a respective limb can be achieved.

According to the invention, this object is achieved by an orthosis having the features of the main claim. Advantageous configurations and developments of the invention are disclosed in the dependent claims, the description and the figures.

In the orthosis having a first fastening element for fastening a first orthosis component on a proximal body part of a user, a second orthosis component having a second fastening element for fastening on a distal body part of the user, and a joint device arranged on the proximal end of the second orthosis component, which has an upper joint part and allows pivoting of the second orthosis component in the sagittal plane relative to the upper part about a joint axis, the upper joint part is formed, or mounted in or on a fastening device thereon, to be pivotable and/or displaceable in the frontal plane and rotationally rigid in the sagittal plane on the first orthosis component. A joint device, which allows pivoting about a joint axis formed by the joint device in the sagittal plane, is arranged or formed on the second orthosis component, for example an upper arm rod or a thigh rod. In order to allow further movements in the case of joints having more than one degree of freedom, the joint device itself is mounted or formed on the first orthosis component on or in a fastening device to be pivotable and/or displaceable with the upper joint part in the frontal plane. In a configuration of the orthosis as a hip orthosis, not only pivoting in the sagittal plane but also pivoting or displacement in the frontal plane are therefore possible for example, so that an adduction or abduction and/or inner rotation and/or outer rotation are made possible or facilitated respectively in a transverse plane. The mounting of the upper joint part itself provides a resistance against pivoting about a pivot axis in the frontal plane, so that an actuator, for example a damper or a drive or another resistance device, may be arranged between the upper joint part and the second orthosis component in order to assist or moderate a movement. The upper joint part is mounted to be displaceable in the frontal plane as an alternative or in addition to pivoting, so that a displacement in the mediolateral direction is possible. It is thereby possible to balance and compensate for relative movements between the first orthosis component and the second orthosis component due to the position of the natural joint at a distance from the joint device.

In one configuration, besides rotatability and/or pivotability in the frontal plane, the upper joint part is also mounted to be displaceable in the proximal-distal direction. A displacement of the upper joint part in the anterior-posterior direction, on the other hand, is prevented. In this configuration, the upper joint part is mounted in a floating fashion on the fastening device and allows a displacement upward or downward, optionally in combination with a displacement away from the body or toward the body in the frontal plane and/or a rotation about the abduction axis and the adduction axis. In this way, for example, the leg can swing forward and backward about the joint axis of the joint device, preferably in a controlled way, and perform an adduction and abduction movement because of the different mounting of the upper joint part on the first prosthesis component, while a displaceable deflection in the walking direction or counter to the walking direction is not possible. By means of this, the association of the first orthosis component and the second orthosis component via the joint device is maintained and the deflection about the joint axis can be influenced.

The upper joint part is in one configuration configured to be flexible in the frontal plane, so that pivoting and/or displacement within the frontal plane is performed by a deformation of the upper joint part per se. The upper joint part is therefore fastened or formed rigidly on the first orthosis component and allows the pivotability and/or displaceability in the frontal plane by a deformation, in particular a resilient deformation, of the upper joint part or of a part of the upper joint part. The deformability may be brought about by a corresponding geometry of the upper joint part, for example by a bellows structure, by a corresponding cross section of the upper joint part or by a multicomponent configuration of the upper joint part with rigid and flexible, in particular resilient, portions.

The upper joint part may be mounted or configured to be rotatable or rotatably rigid in the transverse plane. It is thereby possible for a rotation about the longitudinal axis of the upper joint part, and therefore also of the second orthosis component, to be enabled or blocked. Depending on the intended use of the orthosis, an inner rotation and an outer rotation, for example of the thigh or the upper arm, are thereby enabled or prevented, for example in the event of injuries in order to protect damaged tissue or to avoid undesired loads. In the case of rotatable mounting in the transverse plane, the movement may be moderated or effected by additional devices, for example in order to provide an increased resistance locally, preferably resiliently, or as a function of sensor data, or in order to specify a range of movement for therapeutic reasons, for example in order to guide a limb passively.

In one configuration, the upper joint part itself is configured in multiple parts, so that the properties and functionalities of the upper joint part may be configured more variably. A multipart configuration allows a deflection, for example displacement or pivoting, of the individual constituent parts of the upper joint part relative to one another. The upper joint part may be mounted in a link guide or on a pin along a link guide on the first orthosis component. Different materials may be combined with one another and additional functions may be integrated into the upper joint part. If a plurality of parts of the upper joint part are fastened to one another in an articulated fashion, a pivotability of parts of the upper joint part in the frontal plane or a displaceability within the frontal plane in the upper joint part itself may be achieved as a result. The integration of flexible portions or components allows a compact configuration of the upper joint part with, at the same time, mobility at least of parts of the upper joint part relative to the first orthosis component.

The upper joint part is, in one embodiment, mounted on the fastening device to be resilient in the frontal plane, and in particular prestressed in the medial direction and/or in the lateral direction. For prestressing in the medial direction, the upper joint part is moved or preloaded in the direction of the first orthosis component so that the upper joint part is held inside a guide or on the first orthosis component. This prevents the upper joint part from being separated from the first orthosis component during use, or at least makes it more difficult.

In one embodiment, the upper joint part is mounted on the fastening device on at least one pin or bolt and/or between two lateral guides. The pin may be formed on the upper joint part or fastened thereon, and is mounted and/or guided within a recess or bore inside the first orthosis component. Conversely, a pin may be arranged or formed in the receptacle for the upper joint part on the first orthosis component, which pin engages into a recess of the upper joint part, for example a correspondingly shaped groove, or is gripped at least partially by a correspondingly shaped hook-shaped section of the upper joint part, so that the upper joint part can pivot about the longitudinal axis of the pin. The bolt on the upper joint part may also be configured so to be non-round and may be mounted in a corresponding application face of a fork-like receptacle on the first orthosis component. A link guide may be formed by the arrangement of the link in the upper joint part or in the receptacle for the upper joint part on the first orthosis component.

In one configuration, the upper joint part is configured as a resilient element, so that the pivotability and/or displaceability in the frontal plane is provided by the resilient element itself. Configuring the upper joint part as a resilient element furthermore has, inter alia, the effect that an initial state is automatically resumed after a deformation and cessation of the deforming force.

In one embodiment, a stop for limiting a deflection in the distal direction is formed between the fastening device and the upper joint part. This stop prevents the second orthosis component from moving along the longitudinal extent of the distal limb and being removed or separated from the first orthosis component. A movement in the proximal direction is advantageously allowed, so that adduction and abduction are possible. During an abduction movement, an arm or a leg is moved away from the center of the body, which may necessitate a deflection of the upper joint part in the proximal direction or upward from the receptacle for the upper joint part. An adduction movement, that is to say bringing a body part toward the center of the body, remains possible without restriction up to a particular degree of abduction because of the displaceable mounting of the upper joint part. Only when the stop prevents further deflection in the distal direction either is the deflectability restricted or a resistance opposes further movement, for example by a resilient element, for example a rubber pad.

In one configuration, an actuator and/or energy storage unit is arranged between the upper joint part and the second orthosis component, with which it is possible to influence a movement of the upper joint part relative to the second orthosis component or to perform this movement. The actuator, for example a motor, a brake, a resilient element, a hydraulic and/or pneumatic damper, influences the movement of the orthosis components with respect to one another, in particular the pivoting movement about the joint axis, and/or enables such movements.

In one embodiment, the fastening device is provided with a parallel guide, in which the upper joint part is guided. The parallel guide is configured, for example, as a U-shaped rod in which the correspondingly designed upper joint part is guided to be pivotable and/or displaceable. The parallel guide prevents a deflection in the anterior-posterior direction of the upper joint part relative to the first orthosis component. It may furthermore prevent a rotational degree of freedom about a pivot axis in the frontal plane, in particular about a horizontal pivot axis or in particular a pivot axis running within the frontal plane in an angle range of up to 90° with respect to the horizontal, and thereby may effectively make it possible to influence the pivoting about the joint axis. The parallel guide likewise allows displacement in the proximal-distal direction, optionally as far as a stop which prevents a further deflection or displacement along the longitudinal extent of the parallel guide. The parallel guide furthermore allows displacement within frontal plane, that is to say in the medial direction or lateral direction, without the desired restriction of at least one rotational degree of freedom of the upper joint part within its mounting on the first orthosis component being negated. An abduction movement and/or an adduction movement is also possible in this embodiment.

When the orthosis is configured as a hip orthosis, the first fastening element is configured for fastening the first orthosis component on the torso of the user, while the second fastening element is configured for fastening the second orthosis component on the thigh of the user. When the orthosis is configured as a shoulder orthosis, the first fastening element is configured for fastening the first orthosis component on the upper body of the user, while the second fastening element is configured for fastening the second orthosis component on the upper arm of the user. The first fastening elements are for example a belt, a cuff surrounding the torso, a multipart shell or a bandage, which are applied around the shoulder joint and fixed on the torso by means of belts or bandages or cuffs on the contralateral side. A second fastening element for securing the second orthosis component on the thigh or on the upper arm is for example a buckle, a shell, a belt, a textile or a combination thereof.

Exemplary embodiments of the invention will be explained in more detail below with the aid of the appended figures.

FIG. 1—a perspective representation of a hip orthosis;

FIG. 2—a detail view of a joint device;

FIG. 3—a detail view of a fastening device;

FIG. 4—various views of the hip orthosis according to FIG. 1;

FIG. 5—a schematic representation of the mounting of the upper joint part;

FIG. 6—a variant of FIG. 5;

FIG. 7—a representation of a multipart upper joint part;

FIG. 8—various mounting configurations;

FIG. 9—mounting of the upper joint part on a pin;

FIG. 10—a variant of FIG. 9;

FIG. 11—a variant of FIG. 9 with a hook-shaped upper joint part;

FIG. 12—variants of FIG. 11;

FIG. 13—variants of bolt mounting;

FIG. 14—a variant of FIG. 11 with a deformable upper joint part;

FIG. 15—a variant of FIG. 14;

FIG. 16—a variant with a link in the upper joint part;

FIG. 17—an individual representation of an upper joint part;

FIG. 18—a side view with an upper joint part which is flexible in the frontal plane;

FIG. 19—a front view of a resilient upper joint part;

FIG. 20—a representation of rotatable mounting of the upper joint part;

FIG. 21—a plan view of mounting according to FIG. 20;

FIG. 22—a variant of FIG. 20;

FIG. 23—a variant with an integrally formed resilient upper joint part;

FIG. 24—a front view of FIG. 23;

FIG. 25—a schematic representation of the functionality of the mounting according to FIG. 23;

FIG. 26—a configuration as a shoulder orthosis;

FIG. 27—a side view of FIG. 26;

FIG. 28—a front view of FIG. 26 in two positions;

FIG. 29—a perspective view according to FIG. 28; and

FIG. 30—a variant of FIG. 26 with a resilient upper joint part.

FIG. 1 shows a schematic representation of an orthosis in the form of a hip orthosis having a first orthosis component 10 with a first fastening element 15 for fastening on the torso or pelvis of a user. The first fastening element 15 may for example be configured as a belt, cuff, shell, partial shell, or another device with which the hip orthosis can be secured removably and reappliably on the body of the user. The first orthosis component 10 has a fastening device 11, on or in which a part of a joint device 30 can be secured. The joint device 30 has an upper joint part 40, which in the exemplary embodiment represented is configured in multiple parts. The upper joint part 40 has a mounting part 41, which is connected by means of screws to an upper bearing component 42. The upper bearing component 42 is part of the joint device 30, which has a lower bearing component or joint lower part 32, arranged or formed on which there is a rod compartment in which a second orthosis component 20 is secured releasably by means of screws. The second orthosis component 20 is arranged distally with respect to the first orthosis component 10 and is mounted to be pivotable about a joint axis on the upper joint part 40. In the exemplary embodiment represented, the second orthosis component is a thigh rod 20, at the proximal end 22 of which the joint device 30 is positioned. Arranged distally with respect to the joint device 30, a second fastening element 21 in the form of a thigh cuff or a thigh shell is arranged on the second orthosis component 20 in order to secure the second orthosis component 20 on the thigh. Arranged between the upper joint part 40 and a joint lower part 32, there is an actuator 50 which is mounted with its distal end on the second orthosis component 20 and spans the joint device 30. The proximal end of the actuator 50 is secured on the upper joint part 40 on a bracket. The actuator 50 may be a damper, a drive or an energy storage unit, in particular a resilient element, or a combination thereof.

The second orthosis component 20 may further be followed distally by a third orthosis component (not represented), for example a lower leg rod, which is connected by means of an orthosis knee joint to the lower leg rod. This may likewise be followed by a foot part or a foot support.

FIG. 2 shows the joint device 30 in more detail on an enlarged scale. The mounting part 41 of the multipart upper joint part 40 is configured in the form of a rod and has a box profile, which forms a projection or a heel on its lower side facing toward the body. This projection or heel serves to increase the contact area and may also be omitted. The bearing component 42 together with the joint lower part 32 forms a joint axis 4, which in the fitted state of the hip orthosis lies at the height of the natural hip joint. The positioning of the joint device 30 on the body of the user is advantageously carried out so that the joint axis 4 runs substantially through the natural hip joint, that is to say it is mounted at the height of the natural hip joint in the frontal plane and runs with an orientation perpendicular to the sagittal plane. The joint axis 4 allows the normal forward gait of the user and pivoting of the leg in the sagittal plane in the anterior-posterior direction. FIG. 2 shows the forwardly directed bracket of the upper joint part 40 on the joint device 30 for fastening the actuator 50 (not represented).

FIG. 3 shows an enlarged representation of the first orthosis component 10 with the fastening device 11 for the upper joint part 40. The fastening device 11 has two lateral guides 110, which are aligned substantially parallel to one another and between which the mounting part 41 of the upper joint part 40 is inserted. The first fastening element 15 in the form of a belt or a cuff, on which the first orthosis component 10 is arranged, is only indicated.

FIGS. 1 to 3 show that the upper joint part 40 is not rigidly mounted in the fastening device 11 but allows pivoting and to a certain extent displacement within the frontal plane between the two lateral guides 110. A relative deflection of the upper joint part 40 and, in particular, of the mounting part 41 with respect to the fastening device 11 during abduction and adduction is thereby permitted. A deflection about a rotation axis which corresponds to the longitudinal axis 4 and is oriented substantially parallel thereto is blocked by means of the two lateral guides 110. In the fitted state, the upper joint part 40 is mounted to be rotationally rigid in the sagittal plane on the first orthosis component 10 and thereby allows supporting of the joint lower part 32, or of the second orthosis component 20, in relation to the upper joint part 40 and therefore also in relation to the first orthosis component 10 in the sagittal plane. The joint device 30 together with the actuator 50 can influence a movement of the leg in the sagittal plane and the radius of movement may likewise be restricted, for example by means of stops inside the joint device, should restriction of the hip flexion angle or the extension angle be necessary. By the laterally open configuration of the fastening device 11, it is possible initially to secure the first orthosis component 10 on the torso or the pelvis of the user as proximal body part and subsequently to fix the remaining part of the hip orthosis thereon. A reverse sequence is also possible. The upper joint part 40 is placed or hooked with the mounting part 41 in the fastening device 11 and guided with the inwardly protruding projection between the two lateral guides 110. If the joint axis 4 is positioned individually correctly for the user, the second orthosis component 20 is fixed with the second fastening element 21 on the thigh so that the hip orthosis is correctly arranged.

FIG. 4 shows six different views of movement situations of a hip orthosis. The left two representations show plan views from above in the proximal-distal direction with the joint device 30, which forms a joint axis 4 that runs while being oriented laterally outward at the height of the natural hip joint. The upper joint part 40 is mounted between the two lateral guides 110 in the fastening device 11 on the first orthosis component 10. The belt or buckle for securing on the user is represented indicatively. Besides pivoting about the joint axis 4, a rotation along the longitudinal extent of the thigh is not possible, and an inner rotation or outer rotation of the leg about the hip joint is blocked by means of the lateral guides 110.

The middle two representations of FIG. 4 show a front view of the orthosis with the joint axis 4, the lateral guides 110 and the fastening device 11. In the upper representation, the second orthosis component 20 is in an initial setting, and in the lower representation it is in a position pivoted outward in the frontal plane. The pivoting is not blocked by the mounting in the fastening device 11, which is indicated by the double arrow.

The right two representations show a side view in which it is illustrated that flexion and extension are possible only about the joint axis 4, while deflection of the upper joint part 40 about a pivot axis which is oriented perpendicularly to the sagittal plane in the frontal plane is blocked.

In the embodiment according to FIGS. 1 to 4, two rotational degrees of freedom for the mounting of the upper joint part 40 on the fastening device 11 are blocked, namely about the pivot axis in the sagittal plane and in the transverse plane; pivoting about a pivot axis perpendicular to the sagittal plane in the frontal plane is possible.

The upper joint part 40 may be guided in a longitudinally displaceable fashion in the fastening device 11, and the inwardly protruding projection or the lug on the mounting part 41 may block a displacement in the distal direction, so that in the case of abduction the mounting part 41 can be displaced upward, while in the case of an adduction beyond a standard extent the lug on the mounting part 41 becomes seated on a projection inside the fastening device 11.

FIG. 5 shows a variant of the mounting of the upper joint part 40 in a schematic sectional representation. The fastening arrangement 11 receives the upper joint part 40, for example with a lateral guide. In this embodiment as well, the upper joint part 40 is configured in multiple parts and has a mounting part 41 which is mounted on the first orthosis component 10 while being prestressed in the direction of the first fastening element 15 by means of a spring 46. The mounting part 41 is coupled in a fashion which is articulated about an additional pivot axis 47 to the bearing component 42, on which the lower part (not represented in detail) of the joint device 30 is then mounted to be pivotable. The pivot axis 47 runs orthogonally to the joint axis 4 and inside the sagittal plane, so that an abduction of the second orthosis component 20 with pivoting about the second pivot axis 47 is possible. If transverse forces that bring about a deflection of the mounting part 41 laterally or outward in the frontal plane occur, this movement is counteracted by the spring 46. The stop of the mounting part 41 or the bearing of the mounting part 41 on the side wall of the fastening device 11 prevents the upper joint part 40 from being able to rotate in the sagittal plane.

A variant of the mounting according to FIG. 5 is shown in FIG. 6, in which the mounting part 41 forms a link 43, in the exemplary embodiment as a rectilinear elongate guide hole, in which a pin 44 is guided. The pin 44 may at the same time serve as a stop and limit a deflection in the proximal direction and the distal direction. Depending on the positioning and dimensioning of the mounting part 41 relative to the fastening device 11, in particular the wall next to the body, pivoting of the mounting part 44 about the pin 44 is also possible. Resilient mounting or prestressing into an initial position, for example into a maximum stop position on the proximal end of the link 43 and/or prestressing in the medial direction, are likewise possible. The link 43 need not necessarily be configured in a straight line.

FIG. 7 shows a variant of the upper joint part 40, in which a plurality of identically shaped parts 41, 42 are connected to one another in an articulated fashion. The individual parts 41, 42 are only deflectable relative to one another about precisely one pivot axis, and make it possible that the entire upper joint part 40 can be deflected with the distal components medially and laterally inside the frontal plane, but pivoting in the sagittal plane as well as rotation in the transverse plane are prevented. The parts 41, 42 need not necessarily be identically shaped, and in particular they may have different axial spacings. In the case of two or more parts 41, 42, displacement proximally or distally is additionally possible.

Various forms of a guide or link 13 are shown in FIG. 8, in which links 13 are formed in a side wall or in a lateral guide, as denoted by the references 110 in FIGS. 1 to 4. In the upper representation, the link 13 is represented as a bore in which a pin (not represented) on the upper joint part 40 is guided. The pin may also be smaller than the bore in order to allow a limited movement. The limiting bore also need not necessarily be round. In the central representation, the link 13 is represented as an arcuate groove, and in the lower representation of FIG. 8 as a straight groove which runs with a laterodistal to medioproximal orientation.

FIG. 9 represents a further variant, in which a second orthosis component in the form of a thigh rod is arranged on an upper joint part 40, likewise by means of a joint device 30. The upper joint part 40 is configured in multiple parts, and besides the bearing component 42 has the mounting part 41, which has two laterally protruding pins 44 that bear on a mounting seat on the upper side of the fastening device 11. The fastening device 11 may be configured in the shape of an arc and comprehensively enclose the mounting part 41. For assembly, the mounting part 41 is inserted from above into the free space inside the fastening device 11 and is subsequently connected to the bearing component 42 by means of screws. The mounting part 41 is shown in the right representation of FIG. 9. The pins 44 protrude laterally from the base body of the mounting part 41 and bear on the curved mounting seat. Displaceability is provided upward or in the proximal direction, as are displaceability in the lateral direction and pivoting about the pivot axis which is formed by the pins 44. A rotation in the sagittal plane about an axis in the frontal plane is inhibited.

A variant of the embodiment according to FIG. 9 is shown in FIG. 10, in which the pins 44 no longer have a cylindrical cross section but a contour matched to the contour of the mounting seat. The lower side is rounded but not circular. An increased stability against abduction is thereby provided, and rotation about the longitudinal extent of the leg is prevented. In a similar way to FIG. 9, the fastening device may form a lateral arc next to the body part, for example the pelvis, or alternatively two flanges protruding laterally outward with upwardly curved ends may form the fastening device 11. The two flanges may also form lateral guides.

A variant of FIGS. 9 and 10 is shown in FIG. 11, in which the multipart upper joint part 40 has a hook-shaped mounting part 41 which is hooked into a bolt 14 that is part of the fastening device 11. At the same time, the bolt 14 forms a pivot axis about which the mounting part 41 can pivot during abduction. A rotation of the upper joint part 40 in the sagittal plane is prevented by the weight force of the orthosis and the thereby ensured bearing of the mounting part 41 on the bolt 14, so that reaction forces between the joint lower part 32 and the upper joint part 40 can be absorbed and transmitted via the first orthosis component 10 and the fastening device 11 onto the torso of the user.

The representations in FIG. 12 shows various configurations of the mounting part 41. In the upper representation, the free space for the bolt 14 corresponds substantially to the diameter of the bolt 14, there being a sufficiently large free space between the bent end of the mounting part 41 and the downwardly leading section in order to insert the bolt 14 into the upper, hook-shaped end.

In the lower representation, the free, upper branch extends obliquely downward, so that there is an approximately triangular free space for receiving the bolt 14. Here again, the passage is dimensioned to be sufficiently large so that the mounting part 41 can be hooked in after the first orthosis component 10 has been placed on the torso or the body of the user.

Various cross-sectional shapes of the bolt are shown in FIG. 13; besides a circular-cylindrical configuration, the bolt 14 may also be configured to be semicircular or partially matched to the contour of the mounting part 41.

A variant of the configuration of the mounting part 41 is shown in FIG. 14. Here again, the mounting part 41 is configured in the form of a hook as part of the upper joint part 40. In the upper, bent region, the mounting part 41 has a bellows structure which allows deformation, in particular resilient deformation, when the downwardly protruding inner branch bears on the bolt 14 during pivoting and the outer branch of the mounting part is moved further outward. This situation is shown in the dashed representation and indicated by the arrow. By the material weakenings and the associated bellows structure that is formed, a resilient deformation is possible in this region. In principle, it is also possible to configure the upper joint part 40 or in particular also the mounting part 41 from a plurality of components and from different materials, and to deliberately combine resilient regions with substantially rigid material sections. A controlled deformability, in particular resilient deformability, with defined restoring forces may thereby be implemented.

FIG. 15 shows a perspective view of such a configuration according to FIG. 14. The two lateral guides 110, which protrude outward from a base 12, receive between them the bolts 14 on which the mounting part 41 is placed. The mounting part 41 has a rectangular cross section, so that bearing is ensured over almost the entire length of the bolt 14, which blocks rotation in the sagittal plane. Incorporated in the apex region of the hook-shaped contour, there are material weakenings 410 or resilient components which facilitate or allow pivotability and resilient restoration.

In FIG. 16, instead of mounting which is hooked in or placed on a bolt 14, the mounting part 41 is provided with a link 43 in which the bolt 14 is guided. In order to assemble the orthosis, the bolt 14 is initially removed and the link 43 is subsequently aligned so that the bolt 14 can be reinserted and pushed through the link. The bolt 14 is then fixed on the side walls 110. This allows pivotability and displaceability about the bolt 14, although rotation of the upper joint part 40 in the sagittal plane is blocked. FIG. 16 shows two different shapes of the link 43; besides a curved groove, an overdimensioned bore may also be used as the link 13. As an alternative to reception between two side walls 110, the mounting part 41 may also form two flanges which extend on both sides next to a central body of the fastening device 11 with two pins or bolts 14 protruding laterally outward.

FIG. 17 shows a further variant, in which the mounting part 41 is configured as part of the upper joint part 40 with a plurality of resilient regions or elements 410. Deformability is thereby provided, which allows lateral displacement of the joint lower part 32 and therefore of the entire joint device 30 within the frontal plane, but still prevents rotation in the sagittal plane. Besides releasable fastening of the mounting part 41 on the fastening arrangement 11, the latter may also be formed in one piece so that a part of the upper joint part 40 is formed integrally or configured on the fastening device 11. The bearing component 42, or the joint device 30, may be fastened on the distal end of the mounting part 41.

In FIG. 18, a further variant is represented and shown in a side view. The first fastening element 15 is configured as a belt, which is applied around the pelvis and is positioned on the body, for example by means of a hook and loop fastener. Arranged on the outer side of the fastening device 15, there is a hook and loop fastening region, for example a hooked region, onto which a complementary constituent part of the hook and loop fastener, for example a fabric part, is attached. The mounting part 41 is configured to be flat and is fixed over a relatively large surface region on the hooked part on the fastening device 11. Because of the flat configuration of the mounting part 41, flexibility about pivot axes inside the main extent planes of the mounting part 41 is possible, although rotation about a pivot axis perpendicular to the sagittal plane is blocked, as is indicated by the crossed out double arrow. The bearing component 42 of the upper joint part is fastened on the mounting part 41, so that the joint device 30 is mounted to be pivotable with the joint lower part 32 and the second orthosis component 20. Arranged between the upper joint part 40 and the second orthosis component 20 in the exemplary embodiment, there is an energy storage unit 51 which is configured as a resilient element, for example a spring or an elastomer, so that energy is stored during extension and released again to assist flexion.

FIG. 19 shows a schematic representation of the attachment according to FIG. 17, with the aid of which it may be seen that a deformation about the deformation regions or resilient regions 410 on the fastening device by the mounting part 41 is possible during abduction.

FIG. 20 shows a variant in which, in a similar way to FIGS. 1 to 4, the fastening device has two lateral guides 110 between which the mounting part 41 is mounted. Rotation of the upper joint part 40 in the sagittal plane is thereby effectively avoided. In contrast to the embodiment according to FIGS. 1 to 4, the mounting part 41 is configured to be round so that a rotation about its longitudinal extent is possible, that is to say an inner rotation and an outer rotation of the limb are enabled. There are in this case a longitudinal displaceability in the proximal-distal direction as well as a displaceability in the mediolateral direction and tilting about a substantially horizontal axis running in the anterior-posterior direction.

FIG. 21 shows a plan view of a mounting situation according to FIG. 20; lateral evasion is possible outward or laterally, and facilitated assembly may therefore also be carried out by inserting the mounting part 41 between the lateral guides 110.

FIG. 22 shows a variant of the embodiment according to FIGS. 20 and 21, in which the proximal end of the mounting part 41 has a stop 45 so that deflection in the distal direction is limited, although deflection in the proximal direction inside the lateral guides 110 still remains possible.

FIG. 23 shows a variant with a resilient mounting part 41 having a rectangular cross section, which is integrally formed, materially fastened or otherwise secured on the fastening device 11. The bearing component 42 as part of the joint device 30 is fastened on the mounting part 41. FIG. 24 shows the embodiment in a front view. The upper representation of FIG. 25 shows the functionality of a deflectability of the upper joint part 40, and more precisely of the mounting part 41. Because of the configuration as a panel-like element having a relatively large main face with a relatively small thickness, a high stability may be achieved perpendicular to the main face so that deflection by applying a moment about the axis perpendicular to the sagittal plane within the frontal plane presents scarcely any or no deformation effect, which is indicated in the upper left representation of FIG. 25. Pivoting outward and a rotation in the longitudinal extent of the second orthosis component 20, as shown in the other two upper representations, are possible. The lower representation shows that an abduction movement is ensured with simultaneous blocking of a rotation in the sagittal plane.

FIG. 26 shows an embodiment in the form of a shoulder orthosis. The first orthosis component 10 is fastened on a shoulder to be treated in the form of a cuff or a supporting shell by means of a belt 15 as the first fastening element. The belt 15 is guided along the contralateral side below the armpit and, for example, fixed by means of a hook and loop fastener. There are other fastening options, for example by a plurality of geometrically stable shells, in a similar way to a suit of armor. Arranged on the first orthosis component 10, there is the fastening device 11 in which the upper joint part 40 is guided, as explained for example with the aid of FIGS. 1 to 4. The joint device 30 with a joint axis is arranged at the height of the shoulder joint and allows a pivoting movement of the arm in the sagittal plane. In the embodiment represented, an energy storage unit 51 is arranged between the second orthosis component 20, which is configured as an upper arm rod and is fixed on the upper arm by means of an upper arm cuff as the second fastening element 21, and the upper joint part 40, which facilitates a lifting movement of the arm in the sagittal plane when it is released. In the case of an angular configuration of the mounting part 41, with a corresponding lateral guide, an outer rotation of the arm is not possible. In the case of rotatable mounting of the upper joint part 40 in a similar way to FIG. 20, an outer rotation of the forearm by rotation of the upper arm about its longitudinal extent is possible.

FIG. 27 shows the shoulder orthosis according to FIG. 26 in an individual representation with rotatable mounting of the upper joint part 40 inside the fastening device 11. Here again, it may be seen that a rotation of the mounting of the upper joint part 40 inside the fastening device 11 is not possible in the sagittal plane but the other rotational degrees of freedom are not restricted. The translational degrees of freedom are limited by the two lateral guides, optionally a stop to prevent excessive deflection in the distal direction and the bearing on the body.

Figures 1, 2, 3, 4:
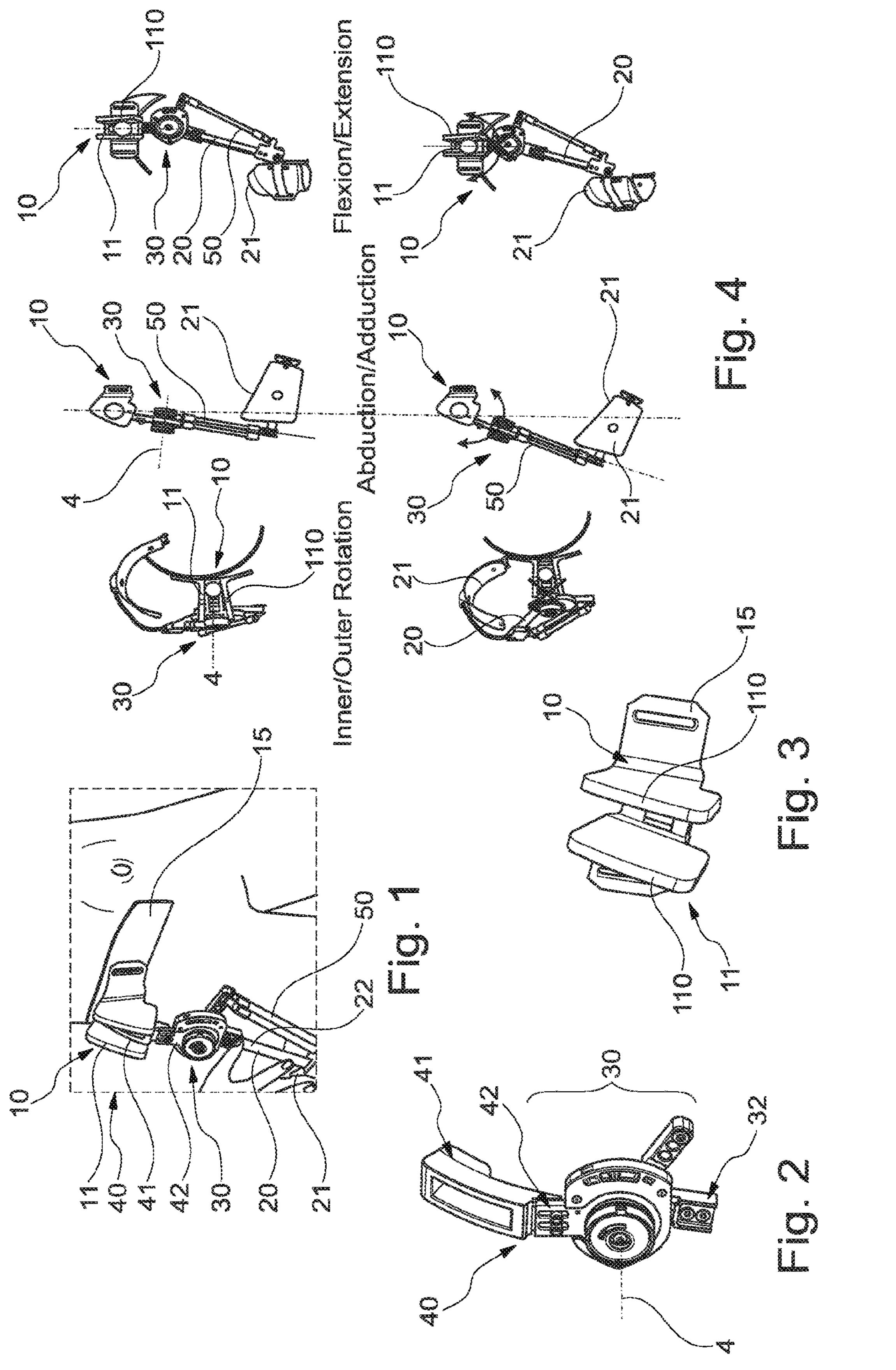
Figure 5:
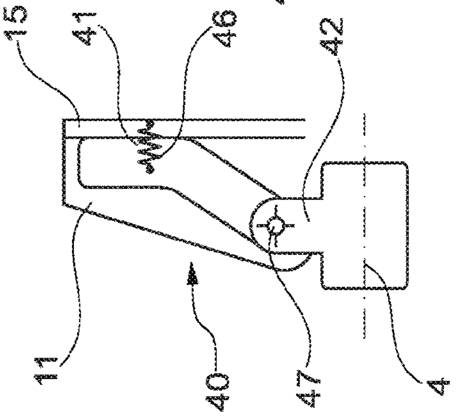
Figure 6:
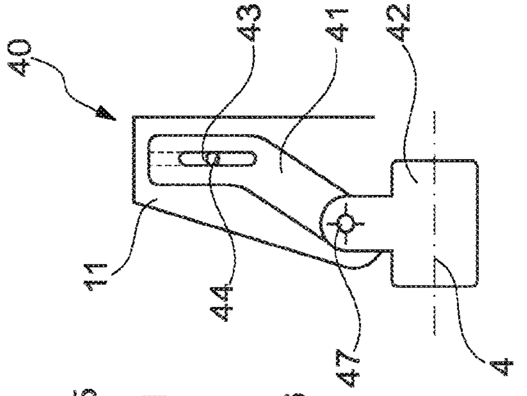
Figure 7:
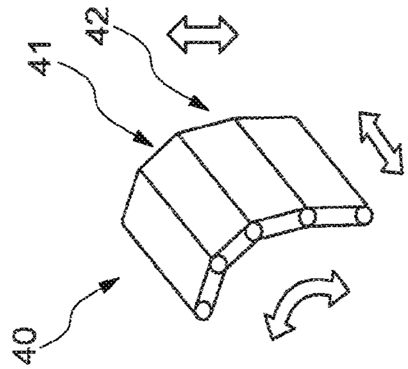
Figure 8:
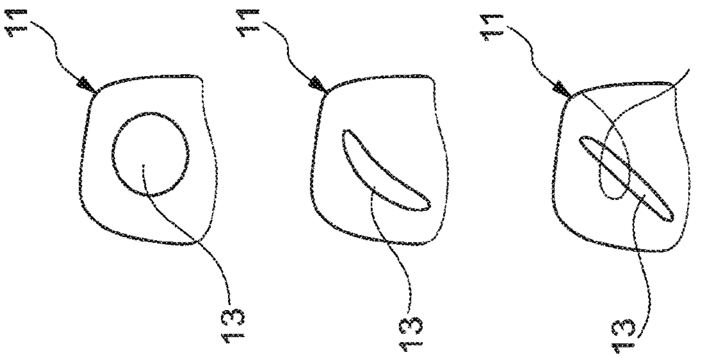
Figure 10:
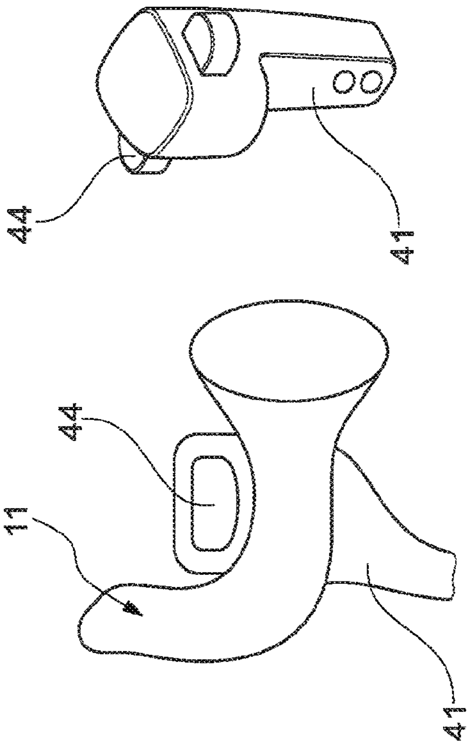
Figure 9:
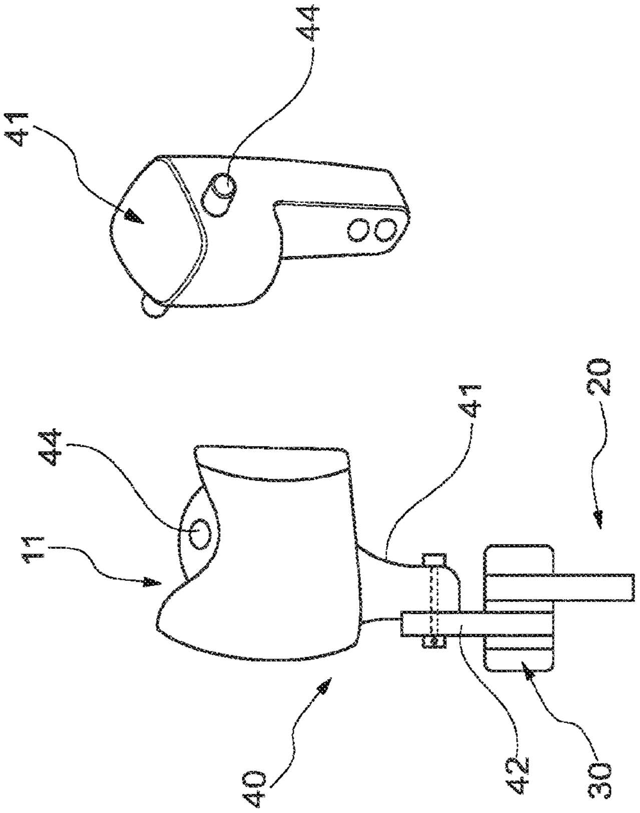
Figures 11, 12, 13, 14:
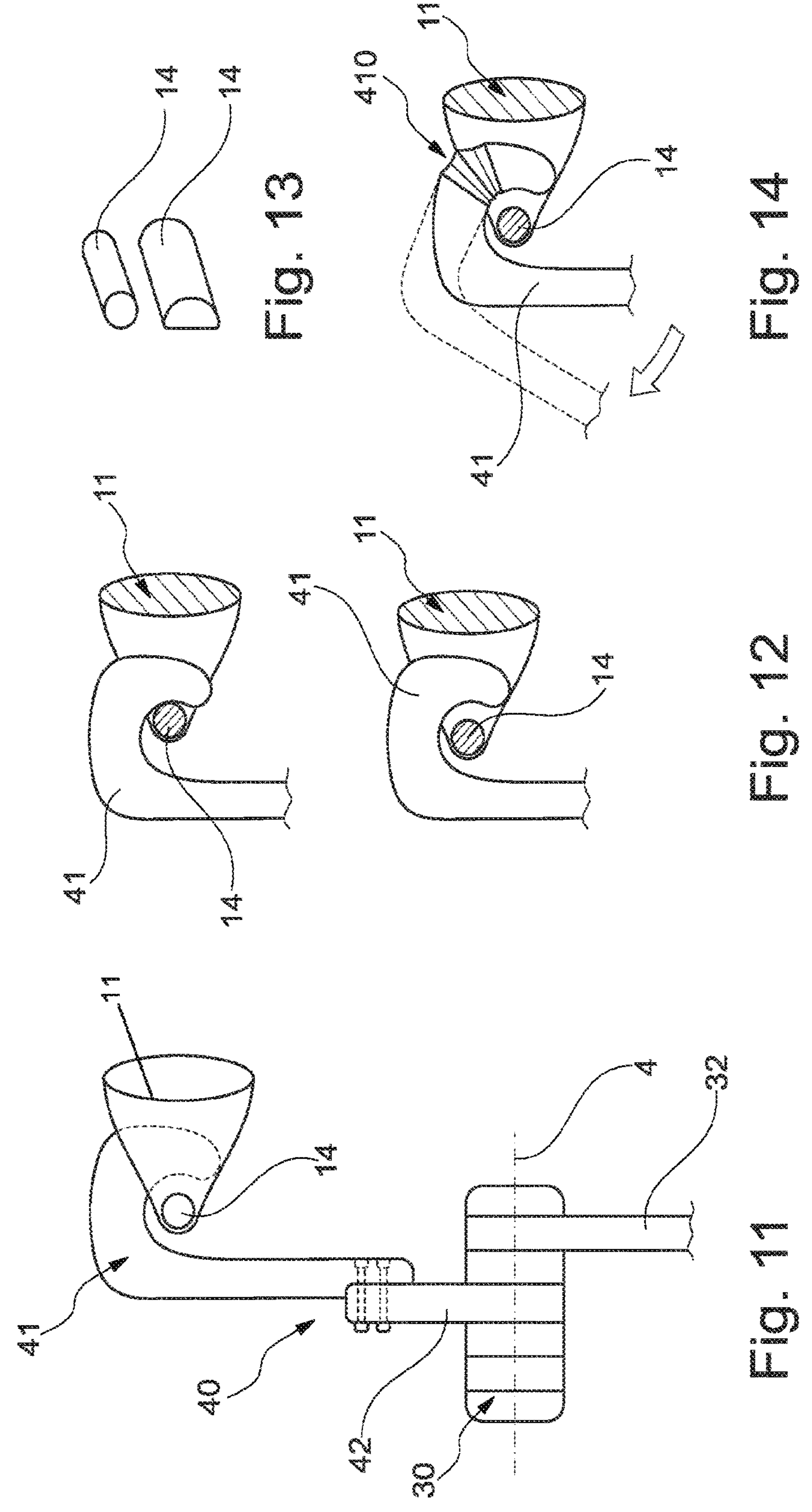
Figure 16:
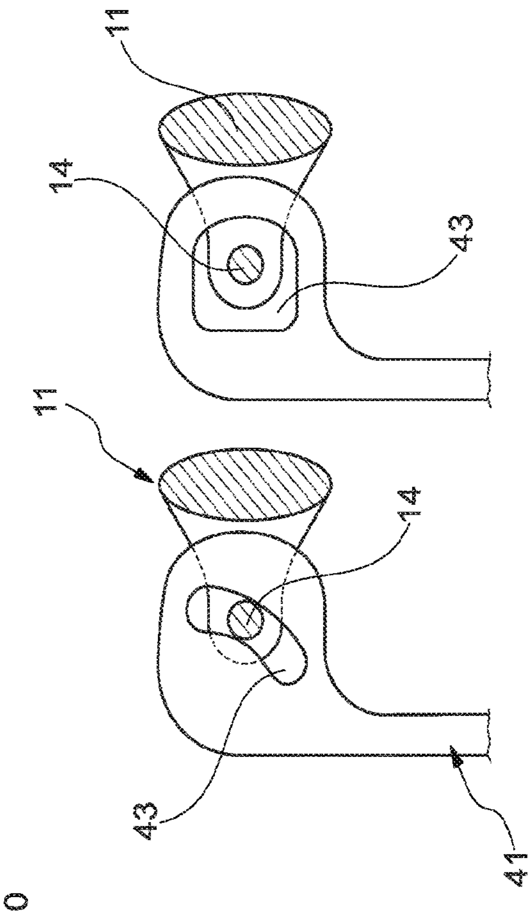
Figure 15:
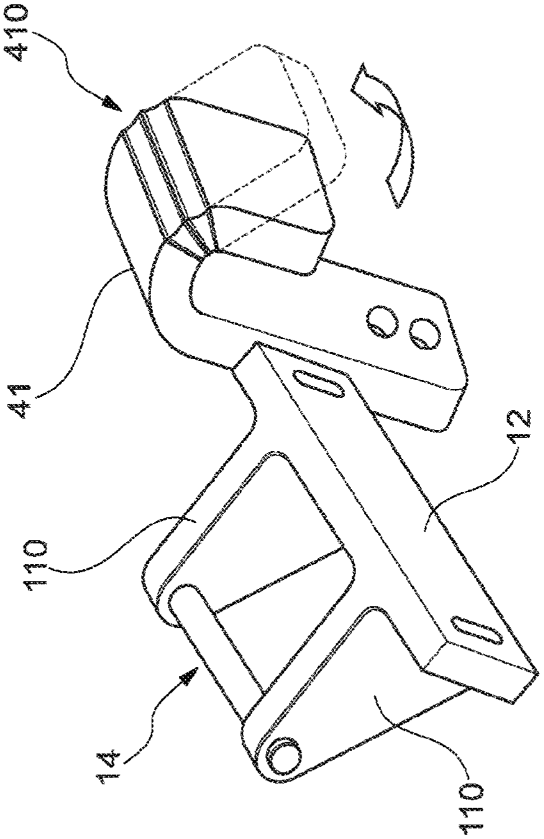
Figure 19:
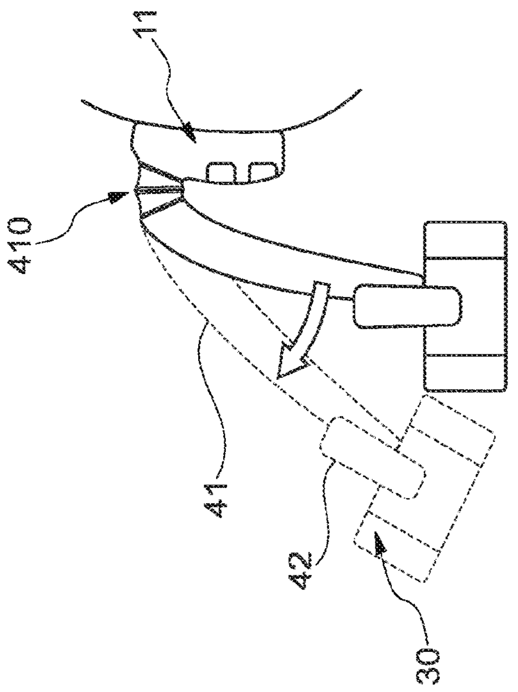
Figure 18:
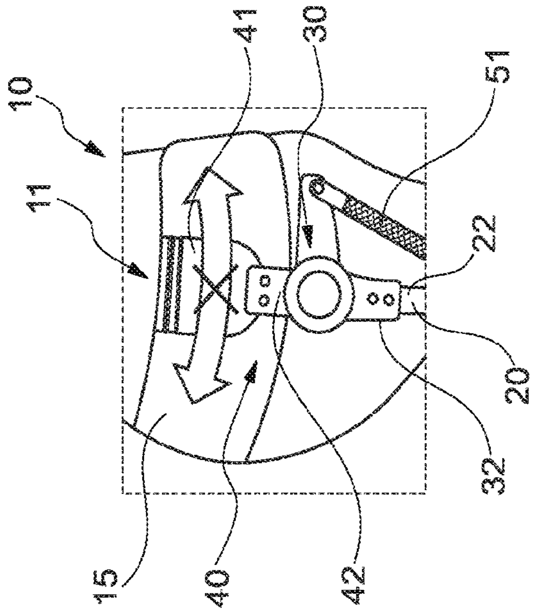
Figure 17:
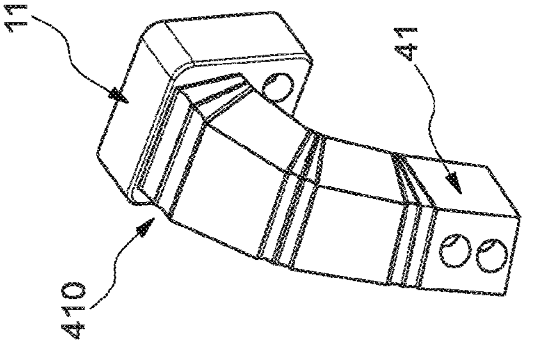
Figure 22:
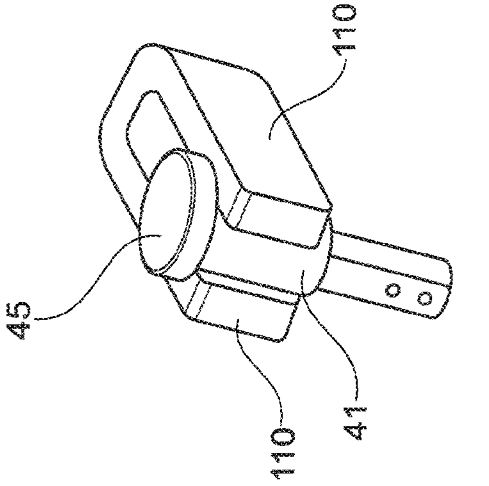
Figure 21:
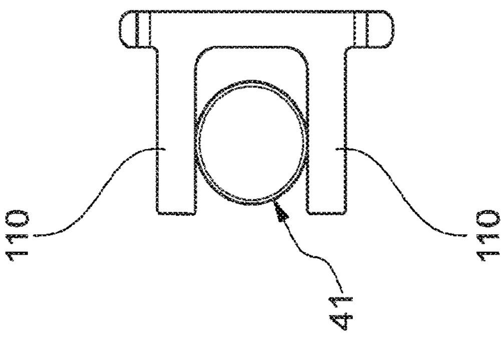
Figure 20:
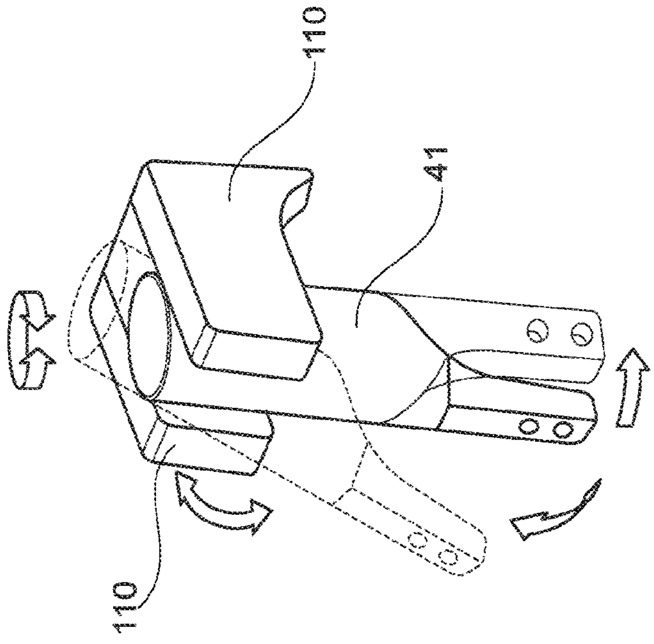
Figure 25:
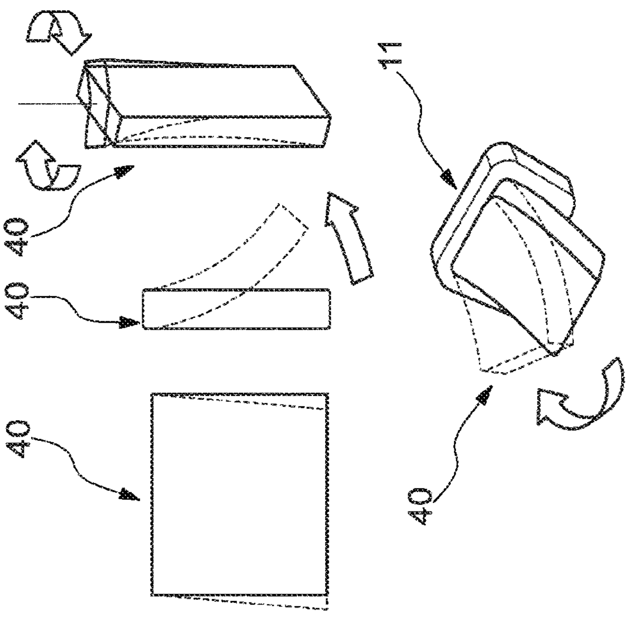
Figure 24:
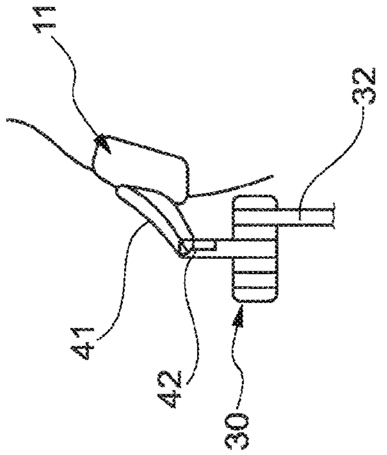
Figure 23:
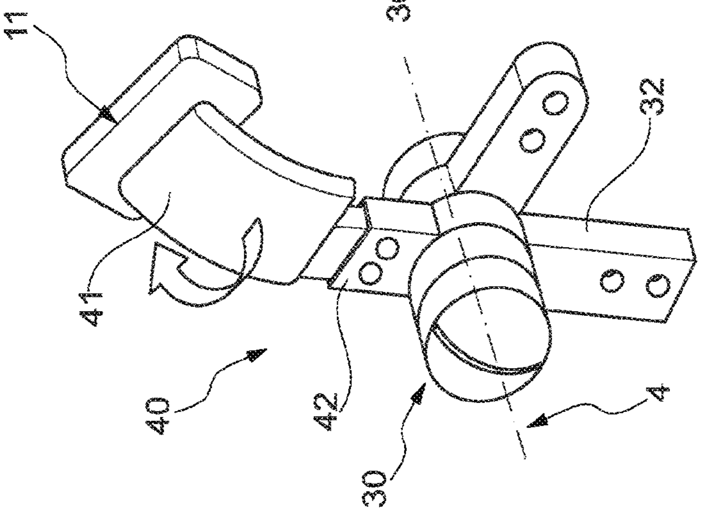
Figure 28:
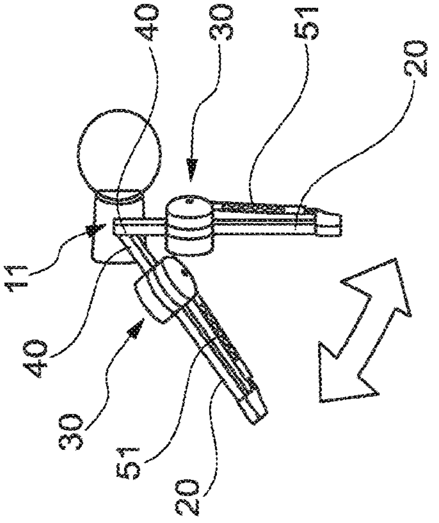
FIG. 28 shows the possible deflectability of the shoulder orthosis according to FIGS. 26 and 27 with the static or almost static fastening device 11 and the possibility of abduction of the upper arm.
Figure 27:
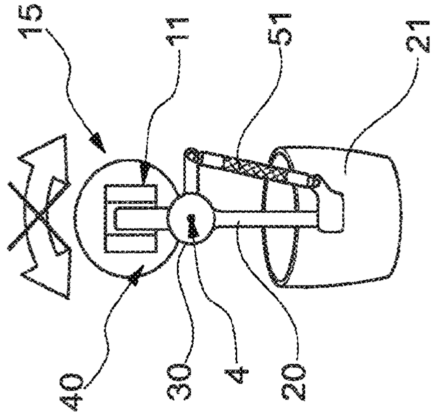
Figure 26:
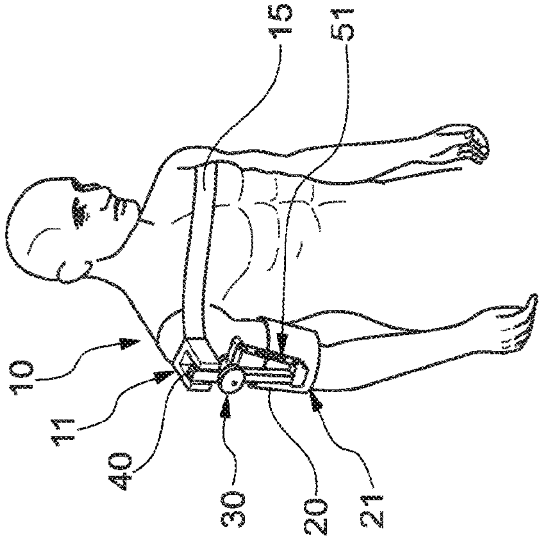
Figure 30:
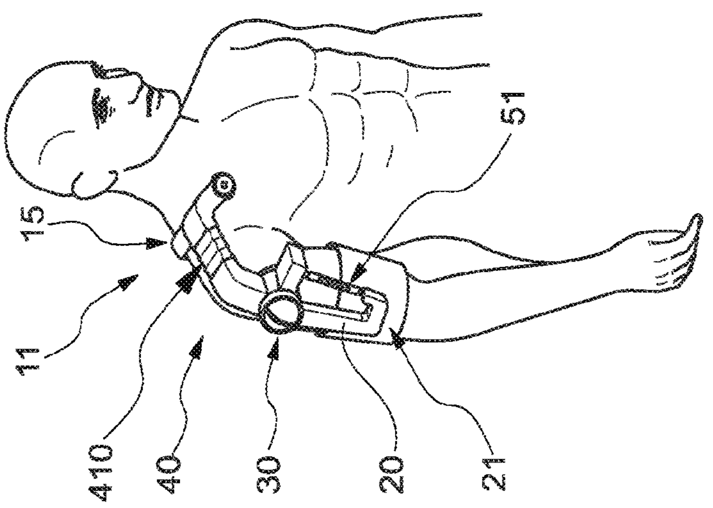
Figure 29:
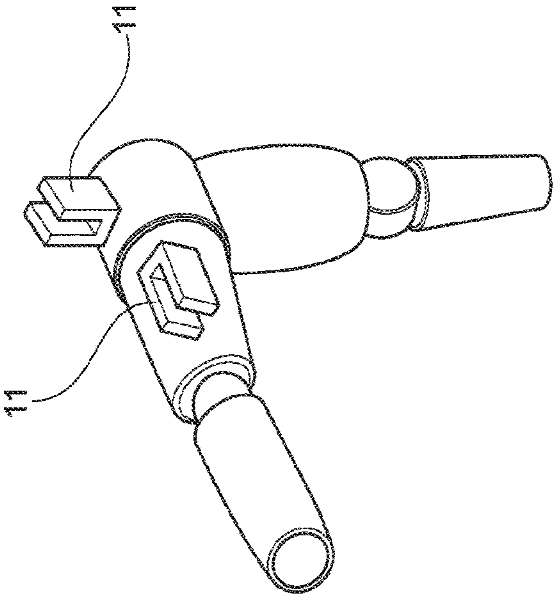
FIG. 29 shows two possible positions of the arm in the configuration of the orthosis as a shoulder orthosis, in which the fastening device 11 is shown first in a buckle-like configuration and opening outward with an arm hanging down, and then with the opening upward with an arm extended horizontally outward.

FIG. 13 a variant of the securing and configuration of the upper joint part 40 with deformation regions or resilient regions 410 formed integrally or configured and an integrally formed fastening device 11, which is formed integrally or fastened on the first orthosis component and can be secured on the torso of the user by means of a fastening element 15 explained with the aid of FIG. 26. Here again, an energy storage unit 51 to assist a lifting movement of the arm is arranged between the upper joint part 40 and the second orthosis component 20. The fixing on the upper arm is carried out by means of the upper arm cuff as the second fastening element 21.

The invention claimed is:

1. An orthosis, comprising:

a first fastening element for fastening a first orthosis component on a proximal body part of a user;

a second orthosis component having a second fastening element for fastening on a distal body part of the user; and a joint device arranged on a proximal end of the second orthosis component, wherein the joint device comprises an upper joint part and allows pivoting of the second orthosis component in a sagittal plane relative to the upper joint part about a joint axis, wherein the upper joint part is placed or hooked in a fastening device between two guides so as to be pivotable and/or displaceable in a frontal plane and to be rotationally rigid in the sagittal plane on the first orthosis component.

2. The orthosis as claimed in claim 1, wherein the upper joint part is mounted to be displaceable in a proximal-distal direction but not be displaceable in an anterior-posterior direction.

3. The orthosis as claimed in claim 1, wherein the upper joint part is configured to be flexible in the frontal plane.

4. The orthosis as claimed in claim 1 wherein the upper joint part is mounted or configured to be rotatable or rotatably rigid in a transverse plane.

5. The orthosis as claimed in claim 1 wherein the upper joint part is configured in multiple parts.

6. The orthosis as claimed in claim 5, wherein a first part and a second part of the upper joint part are fastened to one another in an articulated fashion.

7. The orthosis as claimed in claim 1 wherein the upper joint part is mounted on the fastening device on at least one pin or bolt and/or between two lateral guides.

8. The orthosis as claimed in claim 1 wherein the upper joint part is configured as a resilient element.

9. The orthosis as claimed in claim 1 the upper joint part is mounted on the fastening device to be resilient in a frontal plane.

10. The orthosis as claimed in claim 1 wherein the upper joint part is guided in a link or has a link.

11. The orthosis as claimed in claim 1 further comprising a stop formed between the fastening device and the upper joint part for limiting displacement in a distal direction.

12. The orthosis as claimed in claim 1 further comprising an actuator and/or energy storage unit arranged between the upper joint part and the second orthosis component.

13. The orthosis as claimed in claim 1 wherein the fastening device has a parallel guide in which the upper joint part is guided.

14. The orthosis as claimed in claim 1 wherein the orthosis is configured as a hip orthosis wherein the first fastening element is configured for fastening the first orthosis component on a torso of the user and the second fastening element is configured for fastening the second orthosis component on a thigh of the user.

15. The orthosis as claimed in claim 1 wherein the orthosis is configured as a shoulder orthosis wherein the first fastening element is configured for fastening the first orthosis component on an upper body of the user and the second fastening element is configured for fastening the second orthosis component on an upper arm of the user.

* * * * *